(12) United States Patent
Schambony et al.

(10) Patent No.: US 9,475,918 B2
(45) Date of Patent: Oct. 25, 2016

(54) STABILIZER MIXTURE

(71) Applicant: BASF SE, Ludwigshafen (DE)

(72) Inventors: Simon Schambony, Ludwigshafen (DE); Alban Glaser, Mannheim (DE); Hubert Trauth, Dudenhofen (DE); Manfred Appel, Dernbach (DE); Sylke Haremza, Neckargemuend (DE)

(73) Assignee: BASF SE, Ludwigshafen (DE)

( * ) Notice: Subject to any disclaimer, the term of this patent is extended or adjusted under 35 U.S.C. 154(b) by 510 days.

(21) Appl. No.: 13/874,619

(22) Filed: May 1, 2013

(65) Prior Publication Data

US 2013/0245166 A1 Sep. 19, 2013

Related U.S. Application Data

(62) Division of application No. 12/160,724, filed as application No. PCT/EP2007/050281 on Jan. 12, 2007, now abandoned.

(30) Foreign Application Priority Data

Jan. 13, 2006 (EP) .................................. 06100343

(51) Int. Cl.
*C09K 15/20* (2006.01)
*C08K 5/3435* (2006.01)
(Continued)

(52) U.S. Cl.
CPC ............... *C08K 5/3435* (2013.01); *C08K 5/34* (2013.01); *C07B 63/04* (2013.01);
(Continued)

(58) Field of Classification Search
CPC ..... C07D 211/58; C09K 15/20; C07B 63/04; C09D 7/1241; C09D 7/125
See application file for complete search history.

(56) References Cited

U.S. PATENT DOCUMENTS

| 5,030,670 A | * | 7/1991 | Hess | ..................... C07D 211/46 524/100 |
| 2004/0030009 A1 | | 2/2004 | Gugumus | |
| 2004/0138350 A1 | | 7/2004 | Haremza et al. | |
| 5,710,228 A | | 1/1998 | Krause et al. | |

FOREIGN PATENT DOCUMENTS

| CA | 2 373 013 | 11/2000 | | |
| CA | 2373013 A1 | * 11/2000 | ........... | C08K 5/5399 |

(Continued)

*Primary Examiner* — Richard A Huhn
(74) *Attorney, Agent, or Firm* — Oblon, McClelland, Maier & Neustadt, L.L.P.

(57) ABSTRACT

Suitable stabilizers for organic material are a mixture comprising
A. at least one oligomeric compound, comprising repeat units of the formula (I),

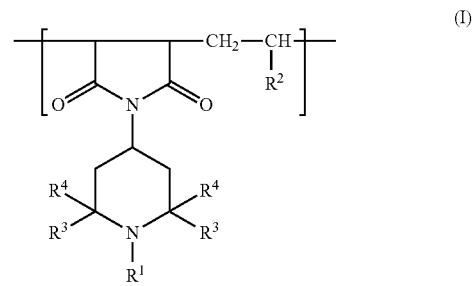

in which the meanings of the symbols are as follows:
$R^1$ is hydrogen, $C_1$-$C_6$-alkyl, formyl, $C_2$-$C_6$-alkanoyl, $C_1$-$C_{12}$-alkoxy, $C_5$-$C_6$-cycloalkoxy, cyanomethyl, 2-hydroxyethyl, benzyl or a radical of the formula —CR'=CH—CO—OR", where
R' is hydrogen, $C_1$-$C_6$-alkyl or a radical of the formula —CO—OR", and
R" is $C_1$-$C_{18}$-alkyl, $C_5$-$C_8$-cycloalkyl, $C_7$-$C_{18}$-aralkyl, phenyl, or tolyl;
$R^2$ is a mixture composed of $C_{14}$-$C_{28}$-alkyl groups, where two of these alkyl groups whose number of carbon atoms is not permitted to differ by more than two respectively make up at least 30% of this mixture;
$R^3$ and $R^4$, independently of one another, are $C_1$-$C_6$-alkyl; and
B. at least one compound of the formula (II) or (III)

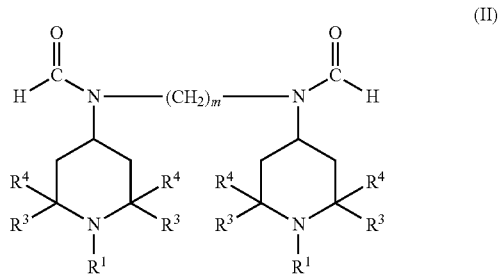

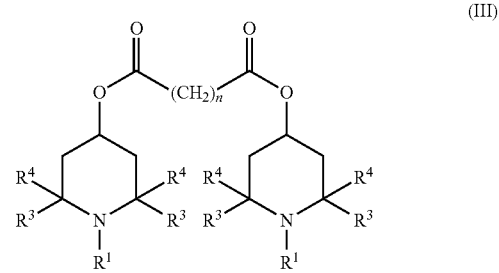

where the meanings of the symbols and indices are as follows:
n and m, independently of one another, are a natural number from 2 to 22, and
$R^1$, $R^3$ and $R^4$, independently of one another, have the meanings given in formula (I).

8 Claims, No Drawings

(51) Int. Cl.
*C08K 5/34* (2006.01)
*C09D 7/12* (2006.01)
*C07D 211/58* (2006.01)
*C07B 63/04* (2006.01)

(52) U.S. Cl.
CPC .................. *C07D 211/58* (2013.01);
*C08K 2201/014* (2013.01); *C09D 7/125* (2013.01); *C09D 7/1241* (2013.01); *C09K 15/20* (2013.01)

(56) References Cited

FOREIGN PATENT DOCUMENTS

| DE | 42 39 437 | 5/1994 |
| EP | 1 413 599 | 4/2004 |
| WO | WO 94/12544 | 6/1994 |
| WO | WO 02/092684 | 11/2002 |

* cited by examiner

STABILIZER MIXTURE

REFERENCE TO PRIOR APPLICATIONS

This application is a Divisional of U.S. application Ser. No. 12/160,724, filed Jul. 11, 2008; which is a 371 of PCT/EP07/50281, filed Jan. 12, 2007. Priority to European patent application 06100343.0 filed Jan. 13, 2006, the entire content of which is incorporated herein by reference.

DESCRIPTION

The invention relates to a mixture composed of oligomeric and monomeric compounds of HALS type, to a process for their preparation, and also to their use as stabilizers for organic material.

Organic material, in particular plastics and paints, is known to decompose very rapidly, especially via exposure to light. This decomposition is usually apparent from yellowing, discoloration, cracking, or embrittlement of the material. Light stabilizers and other stabilizers are therefore intended to achieve satisfactory prevention of decomposition of organic material via light, oxygen, and heat.

Derivatives of 2,2,6,6-tetraalkylpiperidine, termed HALS (Hindered Amine Light Stabilizers), have been used commercially now for about thirty years as light stabilizers and other stabilizers, in particular for plastics and paints.

WO 94/12544 describes maleimide-α-olefin copolymers which have HALS groups as substituents, features of these copolymers being not only the lack of any tendency toward migration within the material to be protected but also good compatibility with the usual types of plastic, and good solubility, and excellent compatibility in the usual paint systems.

Although these compounds are now achieving excellent success in practical commercial use, there is nevertheless room for improvement, in particular with regard to storage properties and transport properties.

It is therefore an object to provide further improved light stabilizers, in particular with improved storage properties and improved transport properties.

The object is achieved via a mixture of the oligomeric HALS described above with certain low-molar-mass (M<1000 g/mol) HALS. The inventive mixture firstly has increased, synergistic stabilizing action and secondly exhibits improved storage properties and improved transport properties, because, unlike the oligomeric compounds alone, it has no tendency toward caking on storage. The inventive mixture does not therefore need to be diluted with diluents, such as fumed silica, silicates, alkaline earth metal stearates, or talc.

Mixtures of oligomeric and low-molecular-weight HALS are previously known, for example in the form of Tinuvin® 791 from Ciba Specialty Chemicals, but these involve structurally different oligomeric compounds which cannot lead to any conclusion concerning any advantageous action of the inventive mixture.

The invention therefore provides a mixture, comprising
A. at least one oligomeric compound, comprising repeat units of the formula (I),

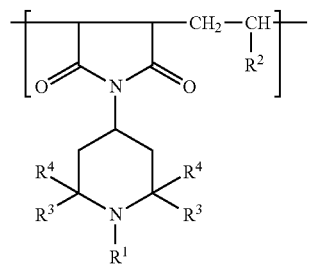

in which the meanings of the symbols are as follows:
$R^1$ is hydrogen, $C_1$-$C_6$-alkyl, formyl, $C_2$-$C_6$-alkanoyl, $C_1$-$C_{12}$-alkoxy, $C_5$-$C_6$-cycloalkoxy, cyanomethyl, 2-hydroxyethyl, benzyl or a radical of the formula —CR'=CH—CO—OR", where
R' is hydrogen, $C_1$-$C_6$-alkyl or a radical of the formula —CO—OR", and
R" is $C_1$-$C_{18}$-alkyl, $C_5$-$C_8$-cycloalkyl, $C_7$-$C_{18}$-aralkyl, phenyl, or tolyl;
$R^2$ is a mixture composed of $C_{14}$-$C_{28}$-alkyl groups, where two of these alkyl groups whose number of carbon atoms is not permitted to differ by more than two respectively make up at least 30% of this mixture;
$R^3$ and $R^4$, independently of one another, are $C_1$-$C_6$-alkyl; and B. at least one compound of the formula (II) or (III)

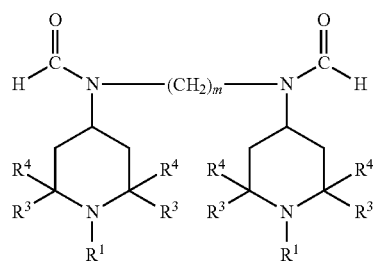

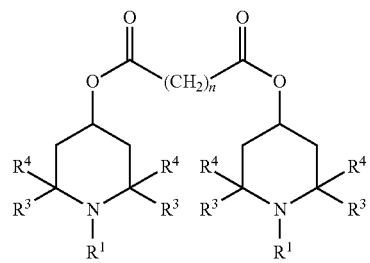

where the meanings of the symbols and indices are as follows:
n and m, independently of one another, are a natural number from 2 to 22,
and
$R^1$, $R^3$ and $R^4$, independently of one another, have the meanings given in formula (I).

The inventive mixtures are used for stabilization of organic material, in particular of polymers, with respect to the effect of light.

The average molecular weight of the oligomers (A) is generally from 1000 to 50 000, preferably from 1500 to 10 000, in particular from 2000 to 5000. The molecular weights given are number-average molecular weights.

The average number of repeat units is from 3 to 100, preferably from 4 to 30, in particular from 5 to 10.

The radical $R^1$ is preferably H, $C_1$-$C_6$-alkyl, formyl, acyl, $C_1$-$C_6$-alkoxy, or benzyl, particularly preferably H, methyl, formyl, acyl or benzyl, in particular H.

The radical $R^2$ is a mixture composed of $C_{14}$-$C_{28}$-alkyl groups, preferably $C_{16}$-$C_{24}$-alkyl groups, in particular $C_{18}$-$C_{22}$-alkyl groups, and the units on which the copolymer is based are therefore $C_{16}$-$C_{30}$ α-olefins, preferably $C_{18}$-$C_{26}$ α-olefins, in particular $C_{20}$-$C_{24}$ α-olefins. $R^2$ is preferably linear alkyl groups.

The presence of a mixture of alkyl groups for $R^2$ means that, when a statistical average is taken across the entire number of all of the copolymer molecules present, two particular alkyl groups whose number of carbon atoms is not permitted to differ by more than two respectively make up at least 30%, preferably respectively make up at least 40%, of this mixture. These are in particular mixtures of 3 particular alkyl groups, e.g. octadecyl, eicosyl, and docosyl, where two of these groups whose number of carbon atoms differs by 2 make up more than 40% of the mixture, and the third group makes up from 3 to 18% of the mixture; other alkyl groups having somewhat fewer than 18 or somewhat more than 22 carbon atoms can be present in the mixture here; their amounts being very small, usually less than 2%.

If not otherwise stated percentages refer to percent by weight.

The radicals $R^3$ and $R^4$ are preferably $C_1$-$C_4$-alkyl, particularly preferably methyl, and the meaning of all of the radicals $R^3$ and $R^4$ is in particular respectively methyl.

Alkyl radicals that can be used and are claimed in the form of $C_1$-$C_6$ (for $R^3$ and $R^4$) and $C_1$-$C_{18}$ (for R") are branched, and in particular straight-chain members of the group, and therefore especially methyl, ethyl, n-propyl, isopropyl, n-butyl, isobutyl, sec-butyl, tert-butyl, n-amyl, isoamyl, sec-amyl, tert-amyl, neopentyl, n-hexyl, n-heptyl, n-octyl, 2-ethylhexyl, 2-propylheptyl, n-nonyl, isononyl, n-decyl, n-undecyl, n-dodecyl, n-tridecyl, isotridecyl, n-tetradecyl, n-pentadecyl, n-hexadecyl, n-heptadecyl, and n-octadecyl.

Straight-chain or branched $C_2$-$C_6$-alkanoyl that can be used for $R^1$ is especially acetyl, but also propionyl, butyryl, isobutyryl, pentanoyl, and hexanoyl.

Especially suitable straight-chain or branched $C_1$-$C_{12}$-alkoxy groups for $R^1$ are $C_6$-$C_8$-alkoxy groups, such as n-hexoxy, isohexoxy, n-octoxy, 2-ethylhexoxy, and isooctoxy, but also methoxy, ethoxy, n-propoxy, isopropoxy, n-butoxy, isobutoxy, sec-butoxy, tert-butoxy, n-pentoxy, n-nonoxy, n-decoxy, n-undecoxy, and n-dodecoxy.

$C_5$-$C_6$-cycloalkoxy groups for $R^1$ are especially cyclopentoxy and cyclohexoxy.

$C_5$-$C_8$-cycloalkyl radicals that can be used for R" are especially cyclopentyl and cyclohexyl, but also cycloheptyl, cyclooctyl, methylcyclopentyl, dimethylcyclopentyl, methylcyclohexyl, ethylcyclohexyl, and dimethylcyclohexyl.

Examples of suitable $C_7$-$C_{18}$-aralkyl radicals for R" are naphthylmethyl, diphenylmethyl, or methylbenzyl, but in particular $C_7$-$C_{18}$-phenylalkyl, such as 1-phenylethyl, 2-phenylethyl, 1-phenylpropyl, 2-phenylpropyl, 3-phenylpropyl, 2-phenylprop-2-yl, 4-phenylbutyl, 2,2-dimethyl-2-phenylethyl, 5-phenylamyl, 10-phenyldecyl, 12-phenyldodecyl, or preferably benzyl.

Tolyl radicals that can be used are ortho-, meta-, and preferably p-tolyl.

An oligomer having the repeat unit (Ia) whose number-average molar mass is from 3000 to 4000 g/mol is particularly preferred as oligomeric component A

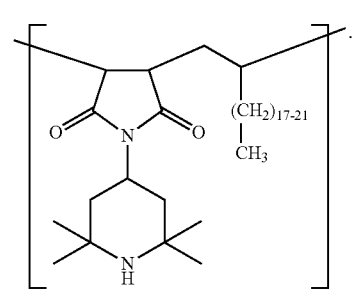

A compound of this type is obtainable as Uvinul® 5050 H from BASF Aktiengesellschaft, Ludwigshafen, Germany.

If the oligomeric component (A) is not obtainable commercially, the compounds can be prepared by the methods given in WO 94/12544.

Among the low-molecular-weight compounds (II) and (III) of component (B), preference is given to those in which the meanings of the symbols and indices are as follows:

$R^1$ is preferably H, $C_1$-$C_4$-alkyl, formyl, acyl, or benzyl, particularly preferably H, methyl, formyl, acyl, or benzyl, especially preferably H.

$R^3$ and $R^4$ are preferably $C_1$-$C_4$-alkyl, particularly preferably methyl, and especially preferably all of the radicals $R^3$ and $R^4$ are methyl.

m and n are preferably a natural number from 4 to 10, particularly preferably 6 or 8, and especially preferably m is the number 6 and n is the number 8.

Preferred are compounds (II) and (III) in which the symbols and indices have the preferred meanings. Particularly preferred are the compounds (II) and (III) in which the symbols and indices have the particularly preferred meanings. Especially preferred are compounds (II) and (III) where the symbols and indices have the especially preferred meanings.

The compounds (IIa), (IIIa), and (IIIb) are particularly preferred as compounds of component (B)

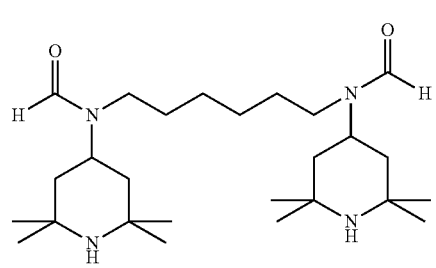

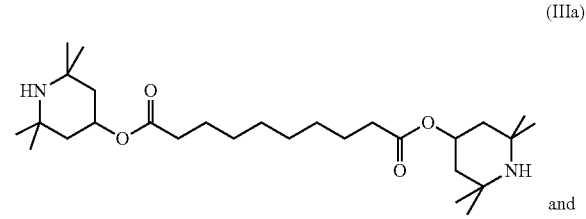

and

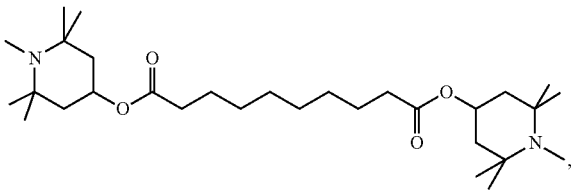
(IIIb)

these being commercially obtainable as Uvinul® 4050 H and Uvinul® 4077 H from BASF Aktiengesellschaft, Ludwigshafen, Germany.

The compound (IIa) is particularly preferred as component B.

If the compounds of the formula (II) are not commercially obtainable, they can be prepared by the methods described in EP-A 0 316 582.

If the compounds of the formula (III) are not commercially obtainable, they can be prepared by methods that are known and familiar to the person skilled in the art, for example via esterification of sebacic esters with 2,2,6,6-tetraalkylpiperidin-4-ol derivatives.

The ratio by weight of components (A) and (B) in the inventive mixtures is generally from 5:1 to 1:5, preferably from 2:1 to 1:2, particularly preferably from 1.2:1 to 1:1.2, and particular preference is given to a mixture whose ratio by weight is about 1:1.

The inventive mixtures can be prepared by processes that are known and familiar to the person skilled in the art.

Component (B) can preferably be added to a melt of component (A), and the mixture can be homogenized, and converted to the desired form, for example pastilles, and allowed to cool.

The invention therefore also provides a respective process for preparation of the inventive mixtures.

However, it is also possible to mix solutions of the two components (A) and (B) and then to remove the solvent(s).

The following combinations of compounds of components (A) and (B) are particularly preferred:
a) the combination of the compounds (Ia) and (IIa),
b) the combination of the compounds (Ia) and (IIIa),
c) the combination of the compounds (Ia) and (IIIb).

The combination (a) is particularly preferred.

The inventive mixtures have excellent suitability for use as stabilizers for stabilization of organic material (preferably not of living organic material) with respect to exposure to light, oxygen, and heat. They are added at a concentration of from 0.01 to 5% by weight, preferably from 0.02 to 1% by weight, based on the organic material, to the organic materials to be stabilized, prior to, during, or after their preparation.

The inventive mixture can be added to the organic material to be protected in the form of a prefabricated mixture of components (A) and (B), but another possibility is separate addition of components (A) and (B) to the material to be protected, in which case the mixture is not produced until the components are present within the material to be protected. In the event of separate addition of components (A) and (B), this can take place simultaneously or non-simultaneously, and the sequence here is not generally significant.

Examples of organic material are cosmetic preparations, such as ointments and lotions, pharmaceutical formulations, such as pills and suppositories, photographic recording material, such as photographic emulsions, or precursors for plastics and paints, but in particular plastics and paints themselves.

The invention also provides an organic material stabilized with respect to exposure to light, oxygen, and heat, in particular a plastic or paint, where the material comprises an inventive mixture, preferably at the concentrations given above.

Any of the known apparatus and methods for mixing to incorporate stabilizers or other additives into polymers can be used for mixing of the inventive mixture, particularly with plastics.

The inventive mixture, or the organic material to be stabilized via the mixture, optionally also comprises at least one further light stabilizer and/or other (co)stabilizers. By way of example, suitable light stabilizers and other (co)stabilizers are those selected from the groups a) to s):
a) 4,4-diarylbutadienes,
b) cinnamates,
c) benzotriazoles,
d) hydroxybenzophenones,
e) diphenylcyanoacrylates,
f) oxamides,
g) 2-phenyl-1,3,5-triazines,
h) antioxidants,
i) nickel compounds,
j) further sterically hindered amines,
k) metal deactivators,
l) phosphites and phosphonites,
m) hydroxylamines,
n) nitrones,
j) amine oxides,
p) benzofuranones and indolinones,
q) thiosynergists,
r) peroxide-destroying compounds and
s) basic costabilizers.

The group a) of the 4,4-diarylbutadienes includes, for example, compounds of the formula (aa)

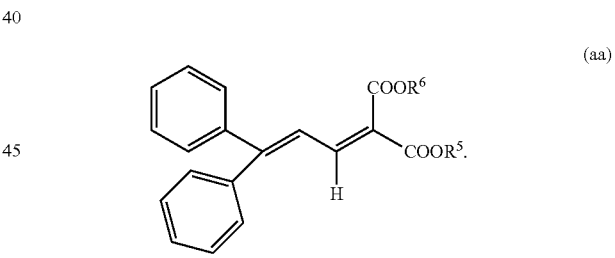
(aa)

The compounds are known from EP-A 916 335. The $R^5$ and/or $R^6$ substituents are preferably $C_1$-$C_8$-alkyl and $C_5$-$C_8$-cycloalkyl.

The group b) of the cinnamates includes, for example, 2-isoamyl 4-methoxycinnamate, 2-ethylhexyl 4-methoxycinnamate, methyl α-(methoxycarbonyl)cinnamate, methyl α-cyano-β-methyl-p-methoxycinnamate, butyl α-cyano-β-methyl-p-methoxycinnamate and methyl α-(methoxycarbonyl)-p-methoxycinnamate.

The group c) of the benzotriazoles includes, for example, 2-(2'-hydroxyphenyl)benzo-triazoles, such as 2-(2'-hydroxy-5'-methylphenyl)benzotriazole, 2-(3',5'-di(tert-butyl)-2'-hydroxyphenyl)benzotriazole, 2-(5'-(tert-butyl)-2'-hydroxyphenyl)benzotriazole, 2-(2'-hydroxy-5'-(1,1,3,3-tetramethylbutyl)phenyl)benzotriazole, 2-(3',5'-di(tert-butyl)-2'-hydroxyphenyl)-5-chlorobenzotriazole, 2-(3'-(tert-butyl)-2'-hydroxy-5'-methylphenyl)-5-chlorobenzotriazole, 2-(3'-(sec-butyl)-5'-(tert-butyl)-2'-hydroxyphenyl)benzotriazole, 2-(2'-hydroxy-4'-octyloxyphenyl)benzotriazole, 2-(3',5'-di(tert-amyl)-2'-hydroxyphenyl)benzotriazole, 2-(3',5'-bis(α,α-dimethylbenzyl)-2'-hydroxyphenyl)benzotriazole, 2-(3'-(tert-butyl)-2'-hydroxy-5'-(2-octyloxycarbonylethyl)phenyl)-5-chlorobenzotriazole, 2-(3'-(tert-butyl)-5'-[2-(2-ethylhexyloxycarbonyl)ethyl]-2'-hydroxyphenyl)-5-chlorobenzotriazole, 2-(3'-(tert-butyl)-2'-hydroxy-5'-(2-methoxycarbonylethyl)phenyl)-5-chlorobenzotriazole, 2-(3'-(tert-butyl)-2'-hydroxy-5'-(2-methoxycarbonylethyl)phenyl)benzotriazole, 2-(3'-(tert-butyl)-2'-hydroxy-5'-(2-octyloxycarbonylethyl)phenyl)benzotriazole, 2-(3'-(tert-butyl)-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-(tert-butyl)-2'-hydroxy-5'-(2-isooctyloxy-carbonylethyl)phenyl)benzotriazole, 2,2'-methylenebis[4-(1,1,3,3-tetramethylbutyl)-6-(benzotriazol-2-yl)phenol], the product of esterification of 2-[3'-(tert-butyl)-5'-(2-methoxycarbonylethyl)-2'-hydroxyphenyl]-2H-benzotriazole with polyethylene glycol 300, [R—CH$_2$CH$_2$—COO(CH$_2$)$_3$]$_2$, where R=3'-(tert-butyl)-4'-hydroxy-5'-(2H-benzotriazol-2-yl)phenyl, and mixtures thereof.

The group d) of the hydroxybenzophenones includes, for example, 2-hydroxybenzophenones, such as 2-hydroxy-4-methoxybenzophenone, 2,2'-dihydroxy-4-methoxybenzophenone, 2,4-dihydroxybenzophenone, 2,2',4,4'-tetrahydroxybenzophenone, 2,2'-dihydroxy-4,4'-dimethoxybenzophenone, 2,2'-dihydroxy-4,4'-dimethoxybenzophenone, 2-hydroxy-4-(2-ethylhexyloxy)benzophenone, 2-hydroxy-4-(n-octyloxy)benzophenone, 2-hydroxy-4-methoxy-4'-methylbenzophenone, 2-hydroxy-3-carboxybenzophenone, 2-hydroxy-4-methoxybenzophenone-5-sulfonic acid and its sodium salt, and 2,2'-dihydroxy-4,4'-dimethoxybenzophenone-5,5'-disulfonic acid and its sodium salt.

The group e) of the diphenylcyanoacrylates includes, for example, ethyl 2-cyano-3,3-diphenylacrylate, which, for example, is obtainable commercially as Uvinul® 3035 from BASF Aktiengesellschaft, Ludwigshafen, 2-ethylhexyl 2-cyano-3,3-diphenylacrylate, which, for example, is obtainable commercially as Uvinul® 3039 from BASF Aktiengesellschaft, Ludwigshafen, and 1,3-bis[[(2'-cyano-3',3'-diphenylacryloyl)oxy]-2,2-bis{[(2'-cyano-3',3'-diphenylacryloyl)oxy]methyl}propane, which, for example, is obtainable commercially as Uvinul® 3030 from BASF Aktiengesellschaft, Ludwigshafen.

The group f) of the oxamides includes, for example, 4,4'-dioctyloxyoxanilide, 2,2'-di-ethoxyoxanilide, 2,2'-dioctyloxy-5,5'-di(tert-but)oxanilide, 2,2'-didodecyloxy-5,5'-di(tert-but)oxanilide, 2-ethoxy-2'-ethyloxanilide, N,N'-bis(3-dimethylaminopropyl)oxamide, 2-ethoxy-5-(tert-butyl)-2'-ethoxanilide and its mixture with 2-ethoxy-2'-ethyl-5,4'-di(tert-but)oxanilide, and also mixtures of ortho- and para-methoxy-disubstituted oxanilides and mixtures of ortho- and para-ethoxy-disubstituted oxanilides.

The group g) of the 2-phenyl-1,3,5-triazines includes, for example, 2-(2-hydroxyphenyl)-1,3,5-triazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-(butyloxy)propoxy)phenyl]-4,6-bis(2,4-dimethylphenyl)-1,3,5-triazine, 2-[2-hydroxy-4-(2-hydroxy-3-(octyloxy)propoxy)phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-(dodecyloxy)propoxy)phenyl]-4,6-bis(2,4-dimethylphenyl)-1,3,5-triazine, 2-(2-hydroxy-4-hexyloxyphenyl)-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine and 2-(2-hydroxyphenyl)-4-(4-methoxyphenyl)-6-phenyl-1,3,5-triazine.

The group h) of the antioxidants comprises, for example:

h.1) alkylated monophenols, for example 2,6-di(tert-butyl)-4-methylphenol, 2-(tert-butyl)-4,6-dimethylphenol, 2,6-di(tert-butyl)-4-ethylphenol, 2,6-di(tert-butyl)-4-(n-butyl)phenol, 2,6-di(tert-butyl)-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di(tert-butyl)-4-methoxymethylphenol, unbranched nonylphenols or nonylphenols which are branched in the side chain, such as, for example, 2,6-dinonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol and mixtures thereof.

h.2) Alkylthiomethylphenols, for example 2,4-dioctylthiomethyl-6-(tert-butyl)phenol, 2,4-dioctylthiomethyl-6-methylphenol, 2,4-dioctylthiomethyl-6-ethylphenol and 2,6-didodecylthiomethyl-4-nonylphenol.

h.3) Hydroquinones and alkylated hydroquinones, for example 2,6-di(tert-butyl)-4-methoxyphenol, 2,5-di(tert-butyl)hydroquinone, 2,5-di(tert-amyl)hydroquinone, 2,6-diphenyl-4-octadecyloxyphenol, 2,6-di(tert-butyl)hydroquinone, 2,5-di(tert-butyl)-4-hydroxyanisole, 3,5-di(tert-butyl)-4-hydroxyanisole, 3,5-di(tert-butyl)-4-hydroxyphenyl stearate and bis(3,5-di(tert-butyl)-4-hydroxyphenyl) adipate.

h.4) Tocopherols, for example α-tocopherol, β-tocopherol, γ-tocopherol, δ-tocopherol and mixtures thereof (vitamin E).

h.5) Hydroxylated thiodiphenyl ethers, for example 2,2'-thiobis(6-(tert-butyl)-4-methylphenol), 2,2'-thiobis(4-octylphenol), 4,4'-thiobis(6-(tert-butyl)-3-methylphenol), 4,4'-thiobis(6-(tert-butyl)-2-methylphenol), 4,4'-thiobis(3,6-di(sec-amyl)phenol) and 4,4'-bis(2,6-dimethyl-4-hydroxyphenyl) disulfide.

h.6) Alkylidenebisphenols, for example 2,2'-methylenebis(6-(tert-butyl)-4-methylphenol), 2,2'-methylenebis(6-(tert-butyl)-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di(tert-butyl)phenol), 2,2'-ethylidenebis(4,6-di(tert-butyl)phenol), 2,2'-ethylidenebis(6-(tert-butyl)-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di(tert-butyl)phenol), 4,4'-methylenebis(6-(tert-butyl)-2-methylphenol), 1,1-bis(5-(tert-butyl)-4-hydroxy-2-methylphenyl)butane, 2,6-bis(3-(tert-butyl)-5-methyl-2-hydroxybenzyl)-4-methylphenol, 1,1,3-tris(5-(tert-butyl)-4-hydroxy-2-methylphenyl)butane, 1,1-bis(5-(tert-butyl)-4-hydroxy-2-methylphenyl)-3-(n-dodecylmercapto)butane, ethylene glycol bis[3,3-bis(3-(tert-butyl)-4-hydroxyphenyl)butyrate], bis(3-(tert-butyl)-4-hydroxy-5-methylphenyl)dicyclopentadiene, bis[2-

(3'-(tert-butyl)-2-hydroxy-5-methylbenzyl)-6-(tert-butyl)-4-methylphenyl]terephthalate, 1,1-bis(3,5-dimethyl-2-hydroxyphenyl)butane, 2,2-bis(3,5-di(tert-butyl)-4-hydroxyphenyl)propane, 2,2-bis(5-(tert-butyl)-4-hydroxy-2-methylphenyl)-4-(n-dodecylmercapto) butane and 1,1,5,5-tetra(5-(tert-butyl)-4-hydroxy-2-methylphenyl)pentane.

h.7) Benzyl compounds, for example 3,5,3',5'-tetra(tert-butyl)-4,4'-dihydroxydibenzyl ether, octadecyl 4-hydroxy-3,5-dimethylbenzylmercaptoacetate, tridecyl 4-hydroxy-3,5-di(tert-butyl)benzylmercaptoacetate, tris(3,5-di(tert-butyl)-4-hydroxybenzyl)amine, 1,3,5-tri(3,5-di(tert-butyl)-4-hydroxybenzyl)-2,4,6-trimethylbenzene, di(3,5-di(tert-butyl)-4-hydroxybenzyl) sulfide, isooctyl 3,5-di(tert-butyl)-4-hydroxybenzylmercaptoacetate, bis(4-(tert-butyl)-3-hydroxy-2,6-dimethylbenzyl) dithioterephthalate, 1,3,5-tris(3,5-di(tert-butyl)-4-hydroxybenzyl) isocyanurate, 1,3,5-tris(4-(tert-butyl)-3-hydroxy-2,6-dimethyl-benzyl) isocyanurate, 3,5-di(tert-butyl)-4-hydroxybenzyl dioctadecyl phosphate and 3,5-di(tert-butyl)-4-hydroxybenzyl monoethyl phosphate, calcium salt.

h.8) Hydroxybenzylated malonates, for example dioctadecyl 2,2-bis(3,5-di(tert-butyl)-2-hydroxybenzyl)malonate, dioctadecyl 2-(3-(tert-butyl)-4-hydroxy-5-methyl-benzyl) malonate, didodecylmercaptoethyl 2,2-bis(3,5-di(tert-butyl)-4-hydroxy-benzyl)malonate and bis[4-(1,1,3,3-tetramethylbutyl)phenyl]2,2-bis(3,5-di(tert-butyl)-4-hydroxybenzyl)malonate.

h.9) Hydroxybenzyl aromatic compounds, for example 1,3,5-tris(3,5-di(tert-butyl)-4-hydroxybenzyl)-2,4,6-trimethylbenzene, 1,4-bis(3,5-di(tert-butyl)-4-hydroxybenzyl)-2,3,5,6-tetramethylbenzene and 2,4,6-tris(3,5-di(tert-butyl)-4-hydroxybenzyl)phenol.

h.10) Triazine compounds, for example 2,4-bis(octylmercapto)-6-(3,5-di(tert-butyl)-4-hydroxyanilino)-1,3,5-triazine, 2-octylmercapto-4,6-bis(3,5-di(tert-butyl)-4-hydroxyanilino)-1,3,5-triazine, 2-octylmercapto-4,6-bis(3,5-di(tert-butyl)-4-hydroxyphenoxy)-1,3,5-triazine, 2,4,6-tris(3,5-di(tert-butyl)-4-hydroxyphenoxy)-1,3,5-triazine, 1,3,5-tris(3,5-di(tert-butyl)-4-hydroxybenzyl) isocyanurate, 1,3,5-tris(4-(tert-butyl)-3-hydroxy-2,6-dimethylbenzyl) isocyanurate, 2,4,6-tris(3,5-di(tert-butyl)-4-hydroxyphenylethyl)-1,3,5-triazine, 1,3,5-tris(3,5-di(tert-butyl)-4-hydroxyphenylpropionyl)-hexahydro-1,3,5-triazine and 1,3,5-tris(3,5-dicyclohexyl-4-hydroxybenzyl) isocyanurate.

h.11) Benzylphosphonates, for example dimethyl 2,5-di(tert-butyl)-4-hydroxy-benzylphosphonate, diethyl 3,5-di(tert-butyl)-4-hydroxybenzylphosphonate ((3,5-bis(1,1-dimethylethyl)-4-hydroxyphenyl)methylphosphonic acid diethyl ester), dioctadecyl 3,5-di(tert-butyl)-4-hydroxybenzylphosphonate, dioctadecyl 5-(tert-butyl)-4-hydroxy-3-methylbenzylphosphonate and calcium salt of 3,5-di(tert-butyl)-4-hydroxybenzylphosphonic acid monoethyl ester.

h.12) Acylaminophenols, for example lauric acid 4-hydroxyanilide, stearic acid 4-hydroxyanilide, 2,4-bisoctylmercapto-6-(3,5-(tert-butyl)-4-hydroxyanilino)-s-triazine and octyl N-(3,5-di(tert-butyl)-4-hydroxyphenyl)carbamate.

h.13) Esters of β-(3,5-di(tert-butyl)-4-hydroxyphenyl)propionic acid with mono- or polyhydric alcohols, such as, e.g., with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

h.14) Esters of β-(5-(tert-butyl)-4-hydroxy-3-methylphenyl) propionic acid with mono- or polyhydric alcohols, such as, e.g., with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2] octane.

h.15) Esters of β-(3,5-dicyclohexyl-4-hydroxyphenyl)propionic acid with mono- or polyhydric alcohols, such as, e.g., with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

h.16) Esters of 3,5-di(tert-butyl)-4-hydroxyphenylacetic acid with mono- or polyhydric alcohols, such as, e.g., with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

h.17) Amides of β-(3,5-di(tert-butyl)-4-hydroxyphenyl)propionic acid, such as, e.g., N,N'-bis(3,5-di(tert-butyl)-4-hydroxyphenylpropionyl)hexamethylenediamine, N,N'-bis(3,5-di(tert-butyl)-4-hydroxyphenylpropionyl) trimethylenediamine, N,N'-bis(3,5-di(tert-butyl)-4-hydroxyphenylpropionyl)hydrazine and N,N'-bis[2-(3-[3,5-di(tert-butyl)-4-hydroxyphenyl]propionyloxy)ethyl] oxamide (e.g. Naugard®XL-1 from Uniroyal).

h.18) Ascorbic acid (vitamin C)

h.19) Aminic antioxidants, such as N,N'-diisopropyl-p-phenylenediamine, N,N'-di(sec-butyl)-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-tolylsulfamoyl)diphenylamine, N,N'-dimethyl-N,N'-di(sec-butyl)-p-phenylenediamine, diphenylamine, N-allyldiphenylamine, 4-isopropoxy-diphenylamine, N-phenyl-1-naphthylamine, N-(4-(tert-octyl)phenyl)-1-naphthylamine, N-phenyl-2-naphthylamine, octylated diphenylamine, e.g. p,p'-di(tert-octyl) diphenylamine, 4-(n-butylamino)phenol, 4-butyrylaminophenol, 4-nonanoylaminophenol, 4-dodecanoylaminophenol, 4-octadecanoylaminophenol, bis(4-methoxyphenyl)amine, 2,6-di(tert-butyl)-4-dimethylaminomethylphenol, 2,4'-diaminodiphenylmethane, 4,4'- diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, mixture of mono- and dialkylated tert-butyl/tert-octyldiphenylamines, mixture of mono- and dialkylated nonyldiphenylamines, mixture of mono- and dialkylated dodecyldiphenylamines, mixture of mono- and dialkylated isopropyl/isohexyldiphenylamines, mixture of mono- and dialkylated tert-butyldiphenylamines, 2,3-dihydro-3,3-dimethyl-4H-1,4-benzothiazine, phenothiazine, mixture of mono- and dialkylated tert-butyl/tert-octylphenothiazines, mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, 2,2,6,6-tetramethylpiperidin-4-one, 2,2,6,6-tetramethylpiperidin-4-ol, the dimethyl succinate polymer with 4-hydroxy-2,2,6,6-tetramethyl-1-piperidinylethanol [CAS number 65447-77-0] (for example Tinuvin® 622 from Ciba Specialty Chemicals Inc.) and the polymer of 2,2,4,4-tetramethyl-7-oxa-3,20-diazadispiro[5.1.11.2]heneicosan-21-one and epichlorohydrin [CAS-No.: 202483-55-4] (for example Hostavin® N 30 from Clariant).

The group i) of the nickel compounds includes, for example, nickel complexes of 2,2'-thiobis[4-(1,1,3,3-tetramethylbutyl)phenols], such as the 1:1 or 1:2 complex, if appropriate with additional ligands, such as n-butylamine, triethanolamine, or N-cyclohexyldiethanolamine, nickel dibutyldithiocarbamate, nickel salts of monoalkyl 4-hydroxy-3,5-di-tert-butylbenzylphosphonates, e.g. the methyl or ethyl ester, nickel complexes of ketoximes, e.g. of 2-hydroxy-4-methylphenyl undecyl ketoxime, nickel complex of 1-phenyl-4-lauroyl-5-hydroxypyrazole, if appropriate with additional ligands.

The group j) of the sterically hindered amines includes, for example, 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) (n-butyl) (3,5-di(tert-butyl)-4-hydroxybenzyl)malonate ((n-butyl)(3, 5-di(tert-butyl)-4-hydroxybenzyl)malonic acid bis(1,2,2,6, 6-pentamethylpiperidyl) ester), condensation product of 1-(2-hydroxyethyl)-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-(tert-octylamino)-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)bis(3,3, 5,5-tetramethylpiperazinone), 4-benzoyl-2,2,6,6-tetramethylpiperidine, 4-stearyloxy-2,2,6,6-tetramethylpiperidine, bis (1,2,2,6,6-pentamethylpiperidyl) 2-(n-butyl)-2-(2-hydroxy-3,5-di(tert-butyl)benzyl)malonate, 3-(n-octyl)-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensation products of N,N'-bis(2,2,6,6-tetramethyl-4-piperidyl)hexamethylenediamine and 4-morpholino-2,6-dichloro-1,3,5-triazine, condensation product of N,N'-bis(2,2,6,6-tetramethyl-4-piperidyl)hexamethylenediamine and formic acid ester (CAS No. 124172-53-8, e.g. Uvinul® 4050 H from BASF Aktiengesellschaft, Ludwigshafen), condensation product of 2-chloro-4,6-bis(4-(n-butyl)amino-2,2,6,6-tetramethylpiperidyl)-1,3,5-triazine and 1,2-bis(3-aminopropylamino)ethane, condensation product of 2-chloro-4,6-di(4-(n-butyl)amino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, mixture of 4-hexadecyloxy- and 4-stearyloxy-2,2,6,6-tetramethylpiperidine, condensation product of N,N'-bis(2,2, 6,6-tetramethyl-4-piperidyl)hexamethylenediamine and 4-cyclohexylamino-2,6-dichloro-1,3,5-triazine, condensation product of 1,2-bis(3-aminopropylamino)ethane and 2,4, 6-trichloro-1,3,5-triazine, as well as 4-butylamino-2,2,6,6-tetramethylpiperidine (CAS Reg. No. [136504-96-6]); N-(2, 2,6,6-tetramethyl-4-piperidyl)(n-dodecyl)succinimide, N-(1,2,2,6,6-pentamethyl-4-piperidyl)(n-dodecyl)succinimide, 2-undecyl-7,7,9,9-tetramethyl-1-oxa-3,8-diaza-4-oxospiro[4.5]decane, reaction product of 7,7,9,9-tetramethyl-2-cycloundecyl-1-oxa-3,8-diaza-4-oxospiro[4.5] decane and epichlorohydrin, 1,1-bis(1,2,2,6,6-pentamethyl-4-piperidyloxycarbonyl)-2-(4-methoxyphenyl)ethene, diester of 4-methoxymethylenemalonic acid with 1,2,2,6,6-pentamethyl-4-hydroxypiperidine, poly[methylpropyl-3-oxo-4-(2,2,6,6-tetramethyl-4-piperidyl)]siloxane, reaction product of maleic anhydride/α-olefin copolymer and 2,2,6, 6-tetramethyl-4-aminopiperidine or 1,2,2,6,6-pentamethyl-4-aminopiperidine, 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxy-4-hydroxy-2,2,6,6-tetramethylpiperidine and a carbon radical of tert-amyl alcohol, 1-(2-hydroxy-2-methylpropoxy)-4-hydroxy-2,2,6,6-tetramethylpiperidine, 1-(2-hydroxy-2-methyl-propoxy)-4-oxo-2,2,6,6-tetramethylpiperidine, bis (1-(2-hydroxy-2-methylpropoxy)-2,2,6,6-tetramethylpiperidin-4-yl) sebacate, bis(1-(2-hydroxy-2-methylpropoxy)-2,2,6,6-tetramethylpiperidin-4-yl) adipate, bis(1-(2-hydroxy-2-methylpropoxy)-2,2,6,6-tetra-methylpiperidin-4-yl) succinate, bis(1-(2-hydroxy-2-methylpropoxy)-2,2,6,6-tetramethyl-piperidin-4-yl) glutarate, 2,4-bis{N-[1-(2-hydroxy-2-methylpropoxy)-2,2,6,6-tetramethylpiperidin-4-yl]-N-butylamino}-6-(2-hydroxyethylamino)-s-triazine, N,N'-bisformyl-N,N'-bis(1, 2,2,6,6-pentamethyl-4-piperidyl)hexamethylenediamine, hexahydro-2,6-bis(2,2,6,6-tetramethyl-4-piperidyl)-1H,4H, 5H,8H-2,3a,4a,6,7a,8a -hexaazacyclopenta[def]fluorene-4, 8-dione (e.g. Uvinul® 4049 from BASF Aktiengesellschaft, Ludwigshafen), poly[[6-[(1,1,3,3-tetramethylbutyl)amino]-1,3,5-triazine-2,4-diyl][(2,2,6,6-tetramethyl-4-piperidinyl) imino]-1,6-hexanediyl[(2,2,6,6-tetramethyl-4-piperidinylimino]] [CAS No. 71878-19-8] or 1,3,5-triazine-2,4,6-triamine, N,N''''-[1,2-ethanediylbis[[4,6-bis[butyl(1,2,2,6,6-pentamethyl-4-piperidinyl)amino]-1,3,5-triazin-2-yl] imino]-3,1-propanediyl]]-bis[N',N''-dibutyl-N',N''-bis(1,2,2, 6,6-pentamethyl-4-piperidinyl)- (CAS No. 106990-43-6) (e.g. Chimassorb 119 from Ciba Specialty Chemicals Inc.).

The group k) of the metal deactivators includes, for example, N,N'-diphenyloxamide, N-salicylal-N'-salicyloylhydrazine, N,N'-bis(salicyloyl)hydrazine, N,N'-bis(3,5-di (tert-butyl)-4-hydroxyphenylpropionyl)hydrazine, 3-salicyloylamino-1,2,4-triazole, the bis(benzylidene) derivative of oxalic dihydrazide, oxanilide, isophthalic dihydrazide, sebacic bisphenylhydrazide, N,N'-diacetyladipic acid dihydrazide, N,N'-bis(salicyloyl)oxalic acid dihydrazide or N,N'-bis(salicyloyl)thiopropionic dihydrazide.

The group I) of the phosphites and phosphonites includes, for example, triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di(tert-butyl)phenyl) phosphite, diisodecyl pentaerythritol diphosphite, bis(2,4-di(tert-butyl)phenyl) pentaerythritol diphosphite, bis(2,6-di(tert-butyl)-4-methylphenyl) pentaerythritol diphosphite, diisodecyloxy pentaerythritol diphosphite, bis(2,4-di(tert-butyl)-6-methylphenyl) pentaerythritol diphosphite, bis(2,4,6-tris(tert-butyl)phenyl) pentaerythritol diphosphite, tristearyl sorbitol triphosphite, tetrakis(2,4-di(tert-butyl) phenyl) 4,4'-biphenylenediphosphonite, 6-isooctyloxy-2,4,8,10-tetra(tert-butyl)dibenzo[d,f][1,3,2]-dioxaphosphepin, 6-fluoro-2,4,8,10-tetra(tert-butyl)-12-methyldibenzo[d,g][1,3,2]dioxa-phosphocin, bis(2,4-di(tert-butyl)-6-methylphenyl) methyl phosphite, bis(2,4-di(tert-butyl)-6-methylphenyl)ethyl phosphite, 2,2',2"-nitrilo[triethyl tris(3,3',5,5'-tetra (tert-butyl)-1,1'-biphenyl-2,2'-diyl) phosphite] and 2-ethylhexyl (3,3',5,5'-tetra(tert-butyl)-1,1'-biphenyl-2,2'-diyl) phosphite.

The group m) of the hydroxylamines includes, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine and N,N-dialkylhydroxylamine from hydrogenated tallow fatty amines.

The group n) of the nitrones includes, for example, N-benzyl-α-phenylnitrone, N-ethyl-α-methylnitrone, N-octyl-α-heptylnitrone, N-lauryl-α-undecylnitrone, N-tetradecyl-α-tridecylnitrone, N-hexadecyl-α-pentadecylnitrone, N-octadecyl-α-heptadecylnitrone, N-hexadecyl-α-heptadecylnitrone, N-octadecyl-α-pentadecylnitrone, N-heptadecyl-α-heptadecylnitrone, N-octadecyl-α-hexadecylnitrone, N-methyl-α-heptadecylnitrone and nitrones derived from N,N-dialkylhydroxylamines prepared from hydrogenated tallow fatty amines.

The group o) of the amine oxides includes, for example, amine oxide derivatives as disclosed in U.S. Pat. Nos. 5,844,029 and 5,880,191, didecylmethylamine oxide, tridecylamine oxide, tridodecylamine oxide and trihexadecylamine oxide.

The group p) of the benzofuranones and indolinones includes, for example, those disclosed in U.S. Pat. Nos. 4,325,863, 4,338,244, 5,175,312, 5,216,052 or 5,252,643, in DE-A-4316611, in DE-A-4316622, in DE-A-4316876, in EP-A-0589839 or in EP-A-0591102 or 3-[4-(2-acetoxyethoxy)phenyl]-5,7-di(tert-butyl)benzofuran-2-one, 5,7-di (tert-butyl)-3-[4-(2-stearoyloxyethoxy)phenyl]benzofuran-2-one, 3,3'-bis[5,7-di(tert-butyl)-3-(4-[2-hydroxyethoxy] phenyl)benzofuran-2-one], 5,7-di(tert-butyl)-3-(4-ethoxyphenyl)benzofuran-2-one, 3-(4-acetoxy-3,5-dimethylphenyl)-5,7-di(tert-butyl)benzofuran-2-one, 3-(3,5-dimethyl-4-pivaloyloxyphenyl)-5,7-di(tert-butyl) benzofuran-2-one, 3-(3,4-dimethylphenyl)-5,7-di(tert-butyl) benzofuran-2-one, Irganoxs HP-136 from Ciba Specialty Chemicals and 3-(2,3-dimethylphenyl)-5,7-di(tert-butyl) benzofuran-2-one.

The group q) of the thiosynergists includes, for example, dilauryl thiodipropionate or distearyl thiodipropionate.

The group r) of the peroxide-destroying compounds includes, for example, esters of β-thiodipropionic acid, e.g. the lauryl, stearyl, myristyl or tridecyl ester, mercaptobenzimidazole or the zinc salt of 2-mercaptobenzimidazole, zinc dibutyldithiocarbamate, dioctadecyl disulfide or pentaerythritol tetrakis(β-dodecylmercaptopropionate).

The group s) of the basic costabilizers includes, for example, melamine, polyvinylpyrrolidone, dicyandiamide, triallyl cyanurate, urea derivatives, hydrazine derivatives, amines, polyamides, polyurethanes, the alkali metal and alkaline earth metal salts of higher fatty acids, e.g. calcium stearate, zinc stearate, magnesium behenate, magnesium stearate, sodium ricinoleate, and potassium palmitate, antimony pyrocatecholate or zinc pyrocatecholate.

The plastic can moreover comprise other additives and added materials. Suitable additives of group t) that can be used are the conventional added materials, e.g. pigments, dyes, nucleating agents, fillers or reinforcing agents, antifogging agents, biocides, and antistatic agents.

Suitable pigments are inorganic pigments, such as titanium dioxide in its three crystalline forms: rutile, anatase, or brookite, ultramarine blue, iron oxides, bismuth vanadates, or carbon black, and also the class of the organic pigments, for example compounds from the class of the phthalocyanines, perylenes, azo compounds, isoindolines, quinophthalones, diketopyrrolopyrroles, quinacridones, dioxazines, indanthrones.

Dyes are any of the colorants which dissolve completely in the plastic used or are present in molecularly dispersed form and therefore can be used to provide high-transparency, non-diffusion coloring of polymers. Other dyes are organic compounds which fluoresce in the visible portion of the electromagnetic spectrum, e.g. fluorescent dyes.

Suitable nucleating agents comprise, for example, inorganic substances, such as talc, metal oxides, such as titanium dioxide or magnesium oxide, phosphates, carbonates, or sulfates, preferably of alkaline earth metals; organic compounds, such as mono- or polycarboxylic acids, and also their salts, e.g. 4-tert-butylbenzoic acid, adipic acid, diphenylacetic acid, sodium succinate, or sodium benzoate; polymeric compounds, such as ionic copolymers ("ionomers").

Suitable fillers or reinforcing materials comprise, for example, calcium carbonate, silicates, talc, mica, kaolin, barium sulfate, metal oxides, metal hydroxides, carbon black, graphite, wood flour, and flours or fibers composed of other natural products, and synthetic fibers. Other examples of fibrous or pulverulent fillers that can be used are carbon fibers or glass fibers in the form of glass textiles, glass mats, or glass silk rovings, chopped glass, glass beads, and also wollastonite. Glass fibers can be incorporated in the form of short glass fibers or else in the form of continuous-filament fibers (rovings).

Examples of suitable antistatic agents are amine derivatives, such as N,N-bis-(hydroxyalkyl)alkylamines or -alkyleneamines, polyethylene glycol esters and polyethylene glycol ethers, ethoxylated carboxylic esters and ethoxylated carboxamides, and glycerolmono- and distearates, and also mixtures of these.

Examples which may be mentioned of plastics which can be stabilized via the inventive mixtures are:
polymers of mono- and diolefins, e.g. low- and high-density polyethylene, polypropylene, linear poly-1-butene, polyisoprene, polybutadiene, and also copolymers of mono- or diolefins, and mixtures of the polymers mentioned;
copolymers of mono- or diolefins with other vinyl monomers, e.g. ethylene-alkyl acrylate copolymers, ethylene-alkyl methacrylate copolymers, ethylene-vinyl acetate copolymers, or ethylene-acrylic acid copolymers;
polystyrene, and also copolymers of styrene or α-methylstyrene with dienes and/or with acrylic derivatives, e.g. styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS), or methyl methacrylate-butadiene-styrene (MBS);

halogenated polymers, e.g. polyvinyl chloride, polyvinyl fluoride, polyvinylidene fluoride, and also their copolymers;

polymers which derive from α,β-unsaturated acids and from their derivatives, e.g. polyacrylates, polymethacrylates, polyacrylamides, and polyacrylonitriles;

polymers which derive from unsaturated alcohols and amines and, respectively, from their acrylic derivatives or acetals, e.g. polyvinyl alcohol and polyvinyl acetate;

polyurethanes, polyamides, polyureas, polyesters, polycarbonates, polysulfones, polyether sulfones, and polyether ketones.

It is also possible to use the inventive mixtures to stabilize paint coatings, e.g. industrial paints. Among these, the following may be especially highlighted: stoved finishes, and among these in turn vehicle finishes, preferably two-layer finishes. Examples of another application sector are paints for exterior painting of buildings, of other structures, or of industrial apparatus.

The inventive mixtures can be in solid or dissolved form when they are added to the paint. Their good solubility in paint systems is a particular advantage here.

The inventive mixtures are preferably used for stabilization of polyamides, and also of ABS polymers and of SAN polymers, in particular of molding compositions derived therefrom, and of paint coatings.

Another preferred application sector is stabilization of low- and high-density polyethylene, and also of polypropylene and polyamide, including, for example, stabilization of fibers derived therefrom.

The examples provide further illustration of the invention but do not restrict it.

EXAMPLES

1. Preparation of an Inventive Mixture 500 g of poly{3-(eicosyltetracosyl)-1-[2,2,6,6-tetramethylpiperidin-4-yl]pyrrolidine-2,5-dione} (CAS No. 152261-33-1; HALS Ia) were melted by heating and mixed with the same amount of N,N'-bisformyl-N,N'-bis(2,2,6,6-tetramethyl-4-piperidinyl)hexamethylenediamine (CAS No. 124172-53-8; HALS IIa). After homogenization, pastilles were formed from the hot mixture and solidified on cooling.

2. Storage Stability of the Inventive Mixture

In order to test tendency toward caking, poly{3-(eicosyltetracosyl)-1-[2,2,6,6-tetramethylpiperidin-4-yl]pyrrolidine-2,5-dione} (CAS No. 152261-33-1; HALS Ia), and also the mixture prepared in example 1, were stored separately at 40° C. in plastic bags. The specimens were assessed visually after 20 h.

| Specimen | | Visual assessment after 20 h at 40° C. |
|---|---|---|
| 1 | HALS Ia | Caking throughout |
| 2 | Mixture composed of HALS Ia and HALS IIa (1:1) | No caking |

The example shows that even under mild conditions the oligomeric component A has a tendency toward caking. In contrast to this, the inventive mixture does not cake.

3. Synergistic Action of the Mixture when Compared with the Individual Components 3a) Weathering of Colored Polypropylene (PP) Plaques Red-colored PP plaques with various HALS stabilizers were produced and then weathered to DIN EN ISO 4892-2. Flexural impact resistance was measured to DIN 53453. The results are shown in the table below:

| | Stabilizer system*) | Flexural impact resistance [mJ/mm$^2$] | | | |
|---|---|---|---|---|---|
| | | 0 h | 2000 h | 3000 h | 4000 h |
| 1 | 3000 ppm HALS IIa | 45 | 45 | 45 | 45 |
| 2 | 1250 ppm HALS Ia 1250 ppm HALS IIa | 45 | 45 | 46 | 45 |
| 3 | 1250 ppm HALS IVa 1250 ppm HALS IVb | 44 | 45 | 42 | 40 |

*)HALS IVa: Polymer composed of 2,2,4,4-tetramethyl-7-oxa-3,20-diaza- dispiro[5.1.11.2]heneicosan-21-one and epichlorohydrin (CAS No. 202483-55-4); HALS IVb: 2,2,4,4-tetramethyl-7-oxa-3,20-diazadispiro[5.1.11.2]heneicosan-21-one (CAS No. 64338-16-5).

From the results it can be seen that the amount of the inventive mixture composed of HALS Ia and HALS IIa (serial No. 2) needed is smaller in order to achieve stabilizing action identical with that achieved with the low-molecular-weight HALS compound IIa alone (serial No. 1). From the third row it can be seen that other mixtures composed of low- and high-molecular-weight HALS compounds have markedly poorer stabilizing action than the inventive stabilizer mixture.

3b) Stabilization of Polypropylene Tapes

Stretched (1:5) tapes composed of polypropylene with various stabilizers were produced and weathered to DIN EN ISO 4892-2. The ultimate tensile strength of the specimens was tested at regular intervals. The specimen was regarded as decomposed as soon as residual ultimate tensile strength was smaller than or equal to 50% of the initial ultimate tensile strength.

| | Stabilizer system*) | Hours to decomposition |
|---|---|---|
| 1 | 1000 ppm HALS Ia | 2800 |
| 2 | 500 ppm HALS Ia 500 ppm HALS IIa | 3200 |
| 3 | 1000 ppm HALS V | 2200 |

*)HALS Ia: poly{3-(eicosyltetracosyl)-1-[2,2,6,6-tetramethylpiperidin-4-yl]pyrrolidine-2,5-dione} (CAS No. 152261-33-1);
HALS IIa: N,N'-bisformyl-N,N'-bis(2,2,6,6-tetramethyl-4-piperidinyl)hexa-methylenediamine (CAS No. 124172-53-8);
HALS V: polymer of 4-hydroxy-2,2,6,6-tetramethyl-1-piperidinylethanol and dimethyl butanedioate

The invention claimed is:

1. A method for the stabilization of organic material with respect to exposure to light, oxygen, and heat, comprising:
mixing (A) and (B) together to form a mixture comprising (A) and (B) in ratio by weight of (A):(B) of 5:1 to 1:5;
storing the mixture;
and then adding the mixture to the organic material, where (A) and (B) are as follows:
(A) at least one oligomeric compound, comprising repeat units of the formula (I),

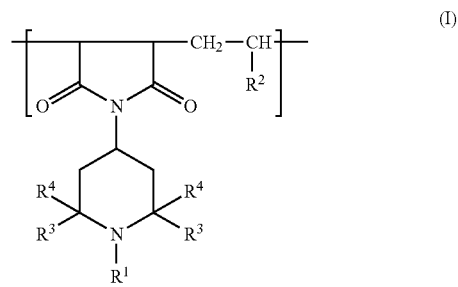

in which the meanings of the symbols are as follows:

$R^1$ is hydrogen, $C_1$-$C_6$-alkyl, formyl, $C_2$-$C_6$-alkanoyl, $C_1$-$C_{12}$-alkoxy, $C_5$-$C_6$-cycloalkoxy, cyanomethyl, 2-hydroxyethyl, benzyl or a radical of the formula—CR'=CH—CO—OR", where R' is hydrogen, $C_1$-$C_6$-alkyl or a radical of the formula —CO—OR", and R" is $C_1$-$C_{18}$-alkyl, $C_5$-$C_8$-cycloalkyl, $C_7$-$C_{18}$-aralkyl, phenyl, or tolyl;

$R^2$ is a mixture composed of $C_{14}$-$C_{28}$-alkyl groups, where two of these alkyl groups whose number of carbon atoms is not permitted to differ by more than two respectively make up at least 30% of this mixture;

$R^3$ and $R^4$, independently of one another, are $C_1$-$C_6$-alkyl; and (B) at least one compound of the formula (II) or (III)

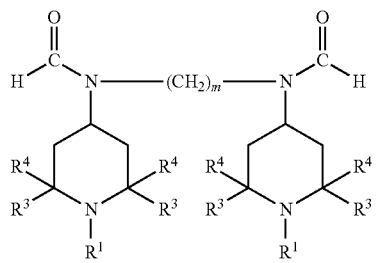
(II)

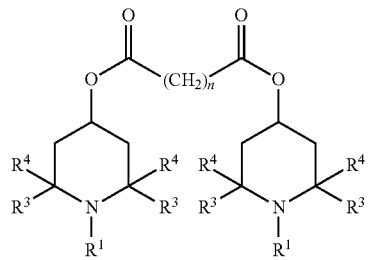
(III)

where the meanings of the symbols and indices are as follows:

n and m, independently of one another, are a natural number from 2 to 22, and $R^1$, $R^3$ and $R^4$, independently of one another, have the meanings given in formula (I).

2. The method according to claim 1, wherein the organic material is a plastic or a paint.

3. The method according to claim 1, where the meanings of the symbols and indices in the formulae (I) to (III) are as follows:

$R^1$ is H, $C_1$-$C_6$-alkyl, formyl, acyl, $C_1$-$C_6$-alkyl or benzyl;

$R^2$ is a mixture composed of $C_{16}$-$C_{24}$-alkyl groups;

$R^3$ and $R^4$ are methyl, and m and n are a natural number from 6 to 8.

4. The method according to claim 1, where component A is an oligomer of the formula (Ia)

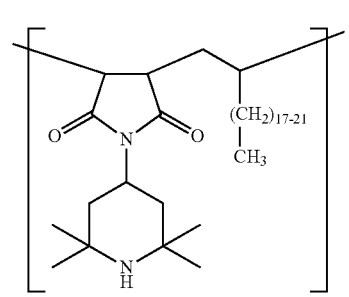
(Ia)

and component B is at least one selected from the group of compounds (IIa), (IIIa), and (IIIb)

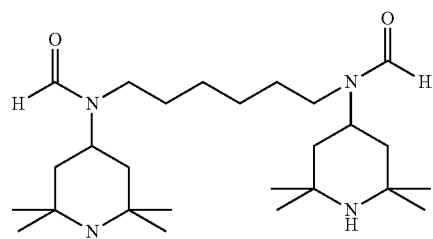
(IIa)

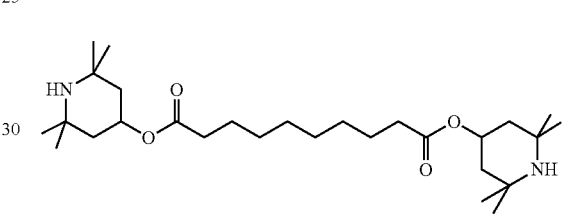
(IIIa)

and

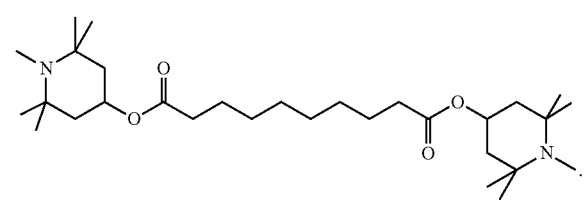
(IIIb)

5. The method according to claim 1, wherein the weight ratio of components A and B is in the range of from 2:1 to 1:2.

6. The method according to claim 1, wherein the weight ratio of components A and B is in the range of from 1.2:1 to 1:1.2.

7. The method according to claim 1, wherein the weight ratio of components A and B is about 1:1.

8. The method according to claim 1, where component A is an oligomer of the formula (Ia)

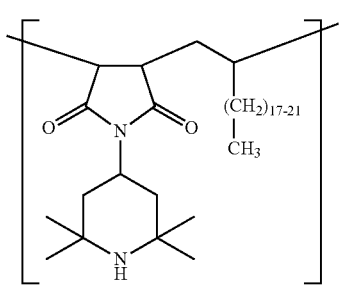
(Ia)

and component B is at least one selected from the group of compounds (IIIa) and (IIIb)
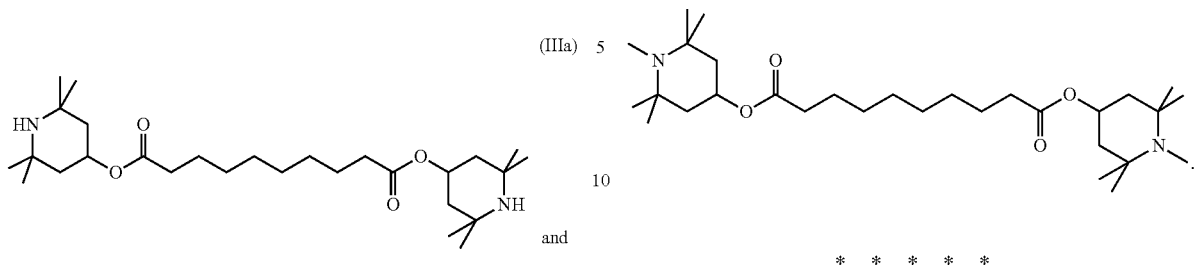
* * * * *